(12) United States Patent
Dodson

(10) Patent No.: US 8,046,241 B1
(45) Date of Patent: Oct. 25, 2011

(54) COMPUTER PAIN ASSESSMENT TOOL

(76) Inventor: William H. Dodson, Odessa, TX (US)

(*) Notice: Subject to any disclaimer, the term of this patent is extended or adjusted under 35 U.S.C. 154(b) by 1005 days.

(21) Appl. No.: 11/702,461

(22) Filed: Feb. 5, 2007

(51) Int. Cl.
*G06Q 50/00* (2006.01)

(52) U.S. Cl. ............................................. 705/2; 705/3

(58) Field of Classification Search ............... 705/2, 3
See application file for complete search history.

(56) References Cited

U.S. PATENT DOCUMENTS

| | | | |
|---|---|---|---|
| 5,533,514 A | 7/1996 | Lavigne et al. | |
| 5,592,947 A | 1/1997 | Lavigne et al. | |
| 5,720,502 A * | 2/1998 | Cain | 283/115 |
| 5,778,882 A * | 7/1998 | Raymond et al. | 600/513 |
| 6,185,517 B1 | 2/2001 | Ohtsu et al. | |
| 6,557,048 B1 | 4/2003 | Keller et al. | |
| 6,690,397 B1 * | 2/2004 | Daignault, Jr. | 715/764 |
| 6,856,315 B2 * | 2/2005 | Eberlein | 345/440 |
| 7,374,536 B1 * | 5/2008 | Taylor | 600/300 |

* cited by examiner

*Primary Examiner* — Gerald J. O'Connor
*Assistant Examiner* — Neha Patel
(74) *Attorney, Agent, or Firm* — Peter V. Schroeder; Booth Albanesi Schroeder LLC

(57) ABSTRACT

A computer assisted pain assessment method where the patient is presented with successive computer screens: a first screen with a human body replica on an interactive touch screen for the patient to shade his or her area of pain being experienced and then presented with a second screen with a color spectrum scale for the patient to select a pain intensity from minimum to maximum by moving a pointer to indicate the pain intensity, a check the box for type of pain where the patient checks a box indicating his or her type of pain, and a gray scale for indicating a depth of pain where the patient moves a pointer between superficial or bone level. Upon completion of these two screens, the next computer screen presents the human body replica with the pain area shown by particular marking for the area of pain, the selected type of pain by a unique pattern for the area of pain and the pattern colored for the particular intensity as selected on the second screen. The patient then is asked to confirm the pain. If confirmed, the patient would activate the finish button on the navigation bar. The patient inputs are processed by the computer along with the patient history and vital statistics, and an on-screen report is available to the clinician or physician to review and print out. A main feature of the report is the Objective Pain Value computed from the area shaded relative to the body replica area and the pain intensity chosen on a color spectrum scale.

10 Claims, 4 Drawing Sheets

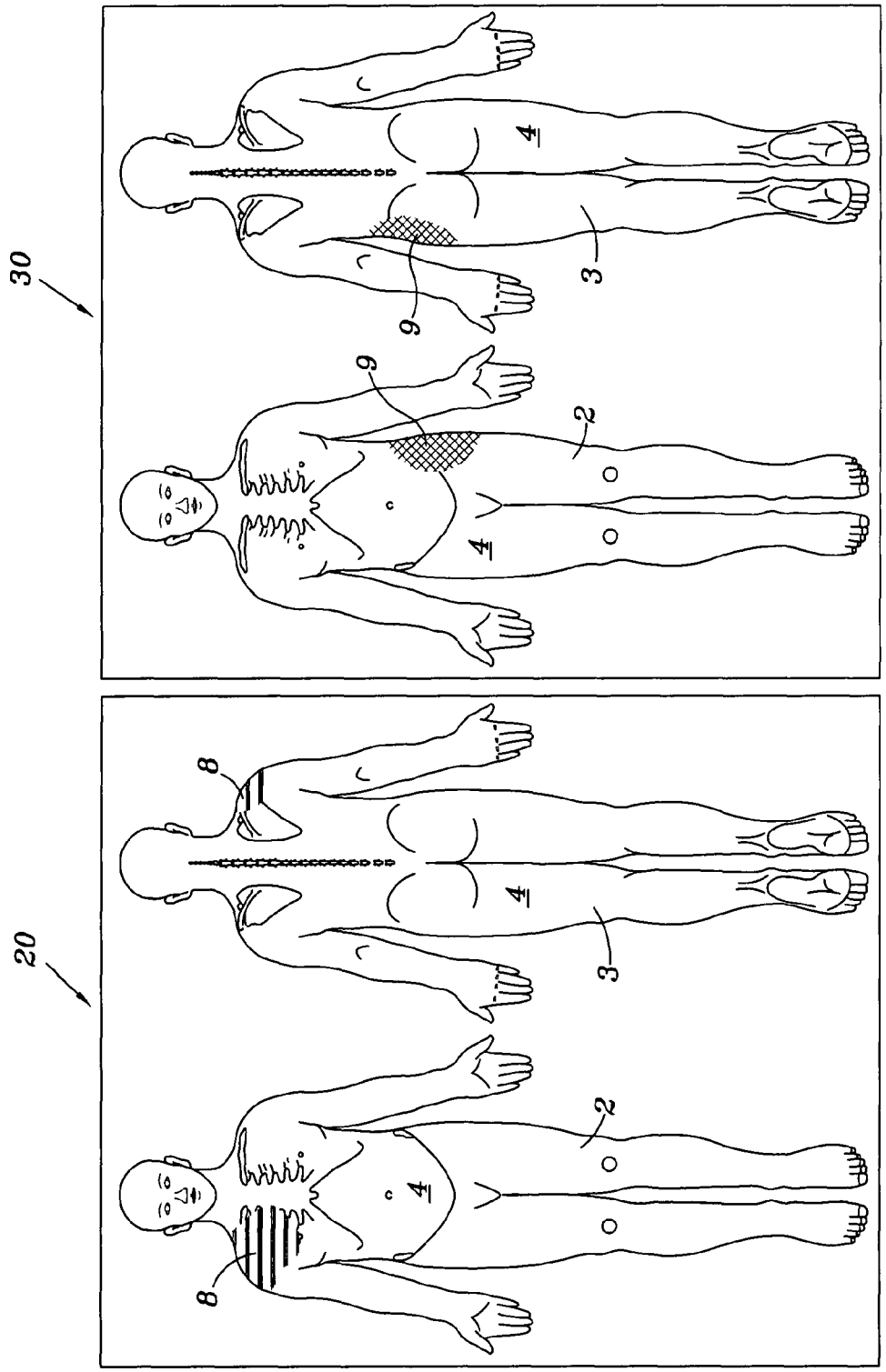

| SURVEY | | | | | | |
|---|---|---|---|---|---|---|
| QUESTIONS | | ANSWERS | | | | |
| PAIN CHANGE: | | 1 | 2 | 3 | 4 | 5 |
| 1) WHEN STANDING ? | | ☐ | ☐ | ☐ | ☐ | ☐ |
| 2) WHEN WALKING ? | *60* | ☐ | ☐ | ☐ | ☐ | ☐ |
| 3) IF LIFTING ? | | ☐ | ☐ | ☐ | ☐ | ☐ |
| 4) DOING PERSONAL HYGIENE ? | | ☐ | ☐ | ☐ | ☐ | ☐ |
| 5) WHILE SITTING ? | | ☐ | ☐ | ☐ | ☐ | ☐ |

LEGEND

1 = LEAST   2 = LESS   3 = UNCHANGED   4 = MORE   5 = MOST

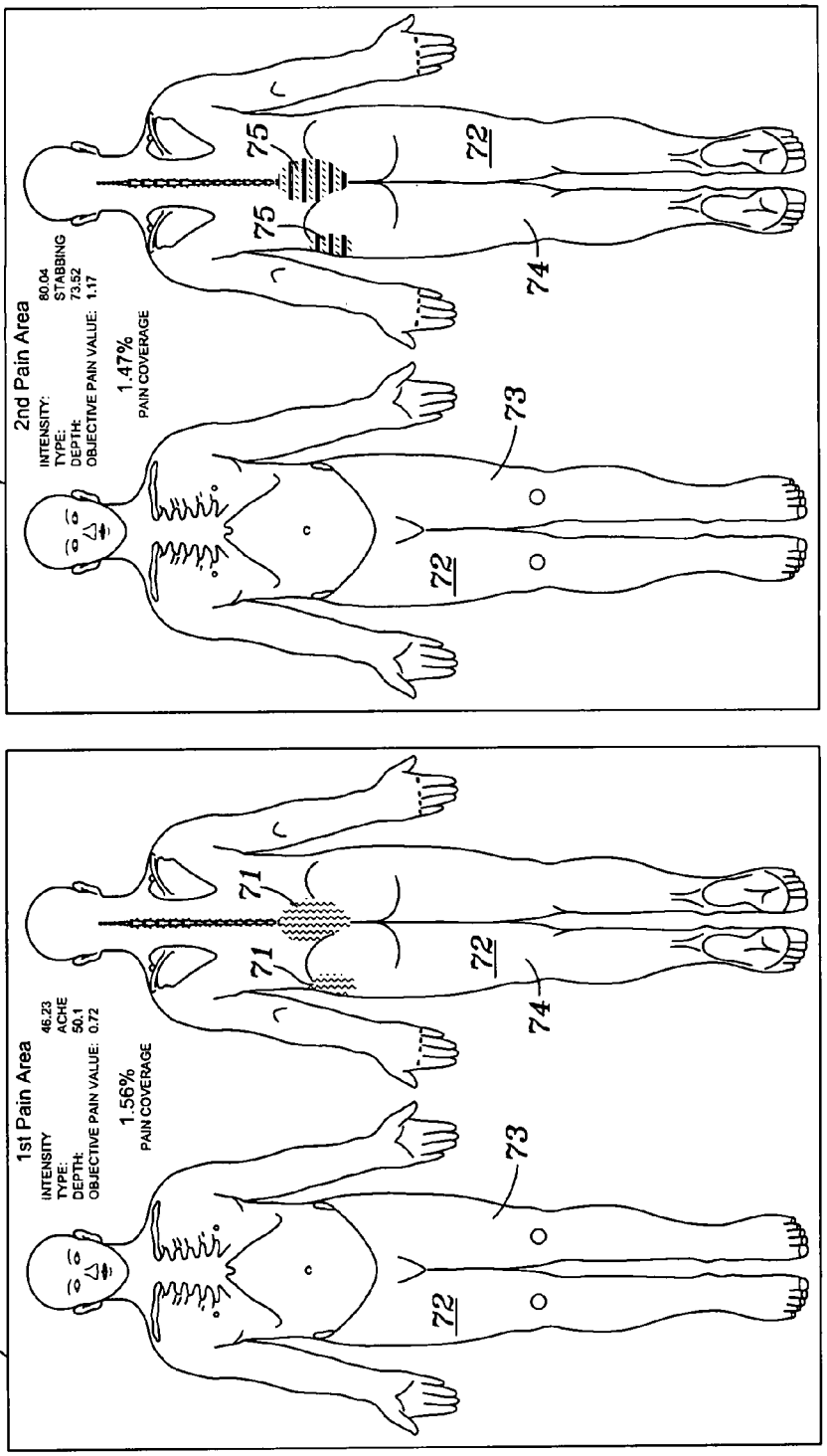

COMPUTER PAIN ASSESSMENT TOOL

BACKGROUND OF THE INVENTION

1. Field of the Invention

The present invention relates to computer systems for documenting human pain and pain intensity, and more particularly to computer pain assessment techniques or tools.

2. Description of Related Art

Bodily pain is a rather subjective, complex phenomenon consisting of a sensorial perception, sometimes revealing a potential or real tissular lesion, and the affective response, such as crying or verbal outburst, provoked by this sensorial perception. As bodily pain sensation is also psychic, objective evaluation thereof is difficult.

Pain evaluation during clinical examination of patients includes evaluation of pain sensitivity and is generally performed by means of palpation of skin or underlying tissues (for example muscles), or by means of other more or less reliable methods. Both the response to manual palpation and evaluation of pain sensitivity from such response is complex and often unreliable, as well as, verbal reports of the patient which are generally unreliable since such reports depend on the patient's recollection of pain, and since bodily pain may widely vary within the same day and from one day to another. It is well known that retrospective symptom data including pain are notoriously inaccurate.

Clinical methods include well known paper pain mapping of the pain area and visual analogue scale of the pain intensity (PPM-VAS). In these methods, patients are presented with paper images of the anterior and posterior of the human body and a finite length scale on paper for indication of no pain or superficial pain at one end to extreme pain at the other end, perhaps on a scale of one to ten or zero to one hundred. The patient colors or shades in the entire area where the pain occurs.

Paper pain mapping includes multiple categories of similar pain words from which the patient checks his or her particular pain associated with the area identified on the drawing of a human anterior and posterior. With most paper pain mapping using various symbols of shading, such as a series of x x x x or o o o o or ^^^, do not allow for several different type pains in the same area of the body. Also, the patient may mark the frequency of recurrence of the pain. Patients with extensive pain areas to shade, such task, using mapping symbols, is tedious and time consuming. If the human body replica is too small, the patient may not be able to shade the exact area of pain.

Using the paper pain mapping and the visual analog scale of intensity it is difficult, if not impossible, to quantify changes in pain perception partly because the area of pain as mapped and the intensity on the visual analog scale are not correlatable.

Lavigne et al., U.S. Pat. No. 5,533,514 describes an algometer system where a representation of a patient's body is displayed on a computer screen and one or more points are marked for pain sensitivity measurement, then a pressure algometer applies pressure at the selected points to the patient's body until the patient perceives the pain threshold of pain (tolerance) and pushes a stop button which holds the pressure applied. Also, the patient selects a pain intensity value on a visual analog scale. These values are stored in the patient's records.

Lavigne et al., in a later U.S. Pat. No. 5,592,947, discloses improvements over the earlier patent that provides a method and an algometer designed for facilitating intensification of the applied pressure at a constant adjustable rate.

The foregoing patents to Lavigne et al., provide for pressure-pain threshold data where palpation examination is more of a sensitivity to pain analysis.

It appears from the early oral and palpation examinations and even paper pain mapping and visual analog scales system, which are heavily subjective, that there is a need for less subjective and more objective clinical inputs from the patient concerning when, where, what and how his or her sensorial perception of pain occurs.

BRIEF SUMMARY OF THE INVENTION

The present invention relates to a computer assisted method for patients suffering from bodily pain to communicate more objectively as to the location, type, area and intensity using a series of computer screens presenting an anterior and posterior of a human body replica, an intensity of pain scale, a type of pain check box, and a depth of pain scale. The patient shades the area on the human body replica where their pain occurs, moves a slider on the intensity of pain scale to the perceived relative intensity of pain, check the type of pain selected that best describes such pain, and move a slider on the depth of pain scale to the perceived relative deepness of the pain. After the patient has completed the last data screen, the patient will be presented with a screen indicating the pain intensity in color matching the patient's choice, the type of pain by the color pattern, and the pain area of the body covered by the color pattern and asking the patient if the drawing accurately describes the pain with choices to change selections, add another pain area and then go to the next screen for a new assessment or exit and finish to save the patient's data.

Another feature of the invention includes modifications of the system to accommodate the clinician or physician definitions of pain, as well as, posing questions with multiple choice answers.

Further, upon the patient's completion of the pain assessment, the computer generates a printable report with the pain type, area and intensity displayed on the body replica and the calculated objective pain value for the doctor or clinician.

In another aspect of the invention, the anterior and posterior of the body replica display has a finite number of pixels, hence, the shading of the body replica by a patient allows calculation of the fraction or percent of the body experiencing pain. The system is designed such that no shading of any area outside the body replica is recorded. Once the patient has selected the intensity of the pain, the system determines an objective pain value. After completion of the pain assessment by the patient, including the type and depth of pain, a full report of the patient's discomfort is available. Such computer retained pain assessment is available for future comparison as to therapeutic pain reduction for the patient.

The present invention provides a simple, more accurate communication by a patient for a doctor or therapist of his or her discomfort by presenting the patient with, in the kiosk or interactive mode, a computer display of the anterior and posterior of a body replica on which the patient shades his or her pain area on the body replica, then a computer display with a color scale (color spectrum) graduated from blue (little or no pain) to red (worst pain) for the patient to select a position on the scale that best indicates the pain intensity, a check-the-box pain type selector, and a depth of pain scale (gray scale) graduated from white to black for superficial to bone deep indication of pain. The pain types for selection by the patient may be preselected by the doctor or therapist, and an additional display or screen may present several multiple choice questions and answers as desired. The patient may repeat the shading and selecting for each different area or pain intensity, type and depth in order to fully describe his or her discomfort. Next, the computer screen displays the body replica with the pain area designated with various symbols coded for the type of pain, and colored for the pain intensity for the patient to review and revise his or her pain assessment or activate finish to save such data and end the pain assessment session.

BRIEF DESCRIPTION OF THE DRAWINGS

FIG. 3 is a computer screen display, (excluding instructions and navigation bar), of the anterior and posterior of a human figure where horizontal bars indicate the type of pain and color of the bars indicates the intensity of pain;

FIG. 4 is similar to FIG. 3 with different pain type and intensity of the same patient;

FIG. 7 is an on screen printable report as to a first area of pain;

FIG. 8 is an on screen printable report as to a second area of pain; and

FIG. 9 is a printable report summary of pain from FIGS. 5 and 6 with an Objective Pain Value assigned.

DETAILED DESCRIPTION OF THE INVENTION

Figure 1:
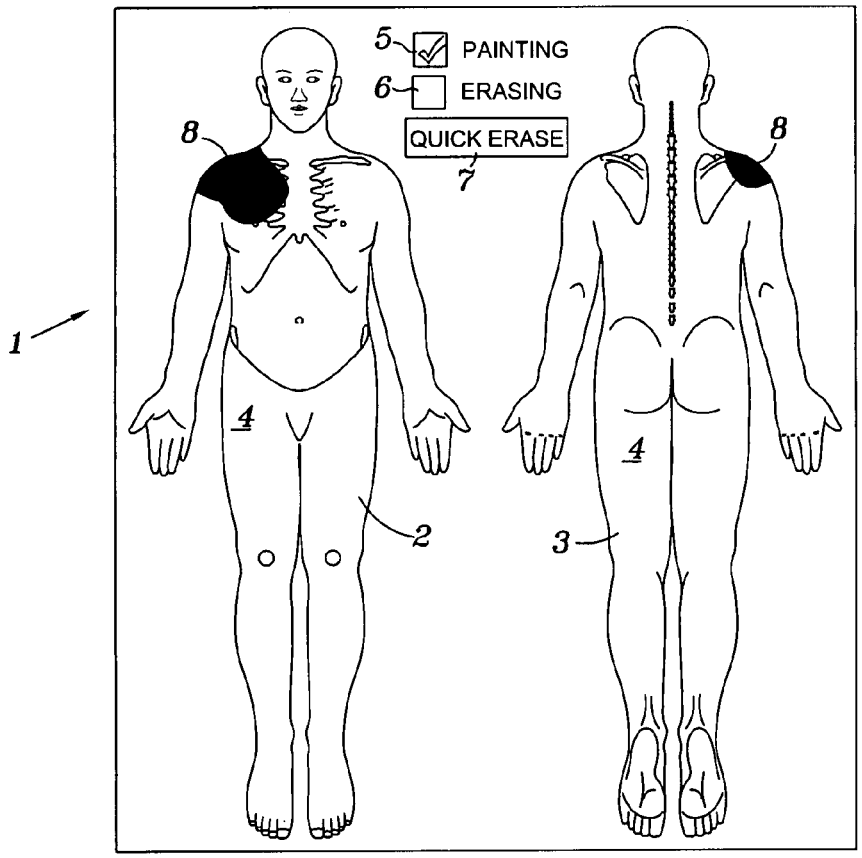
FIG. 1 is a computer screen display, (excluding instructions and navigation bar), of the anterior and posterior of a human figure enclosing a touch screen region for painting or shading an area of pain.

Referring now to the drawings and in particular to FIGS. 1 through 4, portions of the interactive display for patient inputs are displayed. The patients are guided through FIGS. 1 through 4 by instruction on each successive screen displays 1, 10, 20, 30 and further assisted by selecting the help screen on the navigation bar, as well as, selecting the prior screen or the next screen on the navigation bar when applicable. In order to illustrate the patient's computer pain assessment, the help aid on the navigation bar and on screen instructions are not shown in FIGS. 1 through 4 and FIG. 6. Likewise, for simplicity of illustration only, FIGS. 7, 8 and 9, screens 70A, 70B and 70C, respectively, do not display the patient information such as name, social security number, gender, date of birth, physical data, medications, etc., although this information is provided on an actual report.

Once the clinician or physician has recorded all of the patient's personal data and medical history, the computer is placed in the kiosk interactive mode which prevents the operating system from presenting any misleading or distracting information on the screen. The patient is seated in front of a computer, which may be a desktop or tablet computer, where a sequence of computer screens or displays are to be displayed. The patient will be briefly instructed on the use of the computer pain assessment tool (ComPAT™) and told to follow the instructions on each screen in sequence.

With particular reference to FIG. 1, the computer screen area confined by the body outline has a finite number of pixels. The patient taps or clicks box 5 Painting to begin painting by shading area of pain 8 on anterior 2 and posterior 3 of human body replica 4 with a touch screen marker to record areas of pain 8. Only the pixels confined within human body replica 4 can be shaded. The patient may check Erasing 6 to lessen area of pain 8 or check Quick Erase 7 to delete the shaded of area of pain 8 on body replica 4, and start anew. Once the patient completes the painting of area of 8, the percentage of human body replica 4 embraced by areas of pain 8 is determined by the number of pixels shaded divided by the total number of pixels that make up human body replica 4 multiplied by 100, expressed as a percentage, herein sometimes referred to as pain coverage.

After the patient completes drawing pain on screen 1, the patient clicks "next" on the navigation bar (not shown in FIG. 1). The patient is presented with screen or display 10 in FIG. 2 which includes color spectrum 11 for selecting pain intensity from deep blue 12 indicating no pain to red 13 indicating worst pain imaginable. The patient moves pointer A along color spectrum 11 or touches or clicks on color spectrum 11 at a point to position pointer A at the color best representing the pain intensity.

Figure 2:
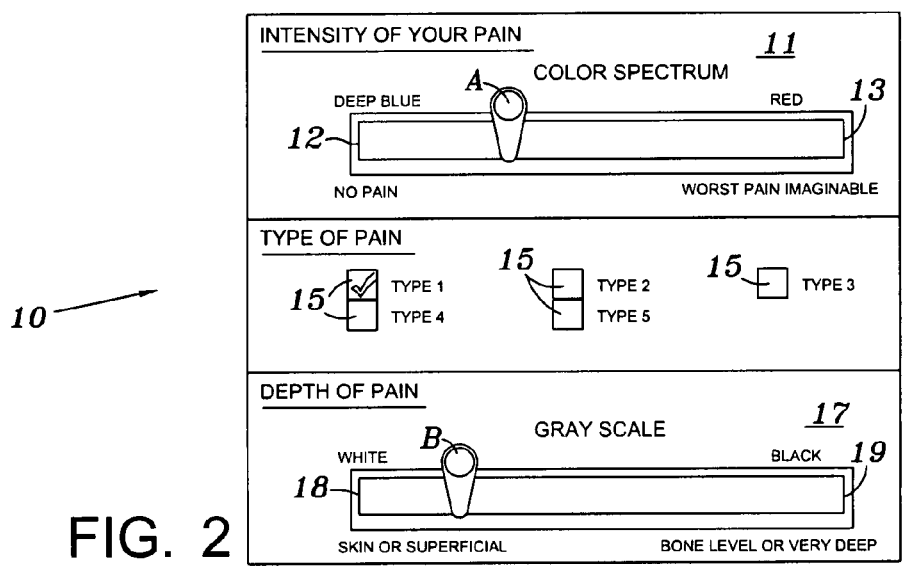
FIG. 2 is a computer screen display, (excluding instructions and navigation bar), of a color spectrum scale for pain intensity, a check box selection of pain type and a gray scale for depth of pain.

The type of pain on screen 10, FIG. 2 consists of five check the boxes 15. Each box 15 would represent a different type of pain. Type 1 through type 5 in FIG. 2 would actually be described on screen 10. The compact pain assessment tool would be preprogrammed by a technician or clinician for each patient depending on the types or kind of pain a patient might expect from the injury, medical procedure or malady the patient experienced, such as ache, stabbing, burning, throbbing, pinching, sharp, radiating, etc. The well known McGill Pain Questionnaire suggests many such types.

The depth of pain is displayed as gray scale 17 on screen 10 for selecting pain depth from white 18 indicating skin or superficial to black 19 indicating bone level or very deep. The patient moves pointer B along the gray scale 17 or touches gray scale 17 to position pointer B anywhere from white 18 to black 19. The data documented on screen 10, FIG. 2 is exclusive for the pain area 8 in FIG. 1.

Further, the patient would click "next" on the navigation bar (not shown in FIG. 2) and be presented with screen 20 and asked to confirm your pain. Screen 20 includes anterior 2 and posterior 3 of human body replica 4, where pain area 8 is delineated by horizontal bars depicting the type of pain and in green from the color spectrum representing the pain intensity. In the on-screen instructions (not shown in FIG. 3), the patient is asked to confirm the pain by checking the "yes" or "no" box (not shown). If the "no" box is checked, pain shading screen 1, FIG. 1 will reappear and the patient can review and modify the pain area previously shaded, then click "next" to bring up screen 10, FIG. 2 to review and modify the description of the pain. When finished with such review and modification, if any, the patient clicks "next" and the confirm pain screen 20, FIG. 3 reappears. The patient would check "yes" to confirm the drawing accurately describes the pain. If the "yes" box is checked, the patient is asked if there are other pain areas to map and/or describe. The patient checks the "yes" or "no" box (not shown). If the patient checks the "yes" box, a second screen like screen 1 would appear for shading a second pain area, then, after shading the second pain area, the patient would click "next" on the navigation bar and a second screen, like screen 10, FIG. 2, would appear for the patient to describe the pain. This description would be exclusive to the second pain area. After describing the second pain area, the patient would click "next" on the navigation bar (not shown), then be presented with screen 30 in FIG. 4, for the second pain area and asked to confirm the pain, the same as done for screen 20 in FIG. 3.

Upon viewing the confirm pain screen 20, FIG. 3 for the first pain area or screen 30, FIG. 4 for the second pain area, if the patient checks the "no" box for the first pain area, screen 1, FIG. 1 would reappear for changes, then in sequence the patient would click "next" and screen 10, FIG. 2 would reappear for changes, then screen 20, FIG. 3 would reappear to confirm the pain, as modified. The first pain must be confirmed (screen 20, FIG. 3) before a second pain area can be selected.

Figures 5, 6:
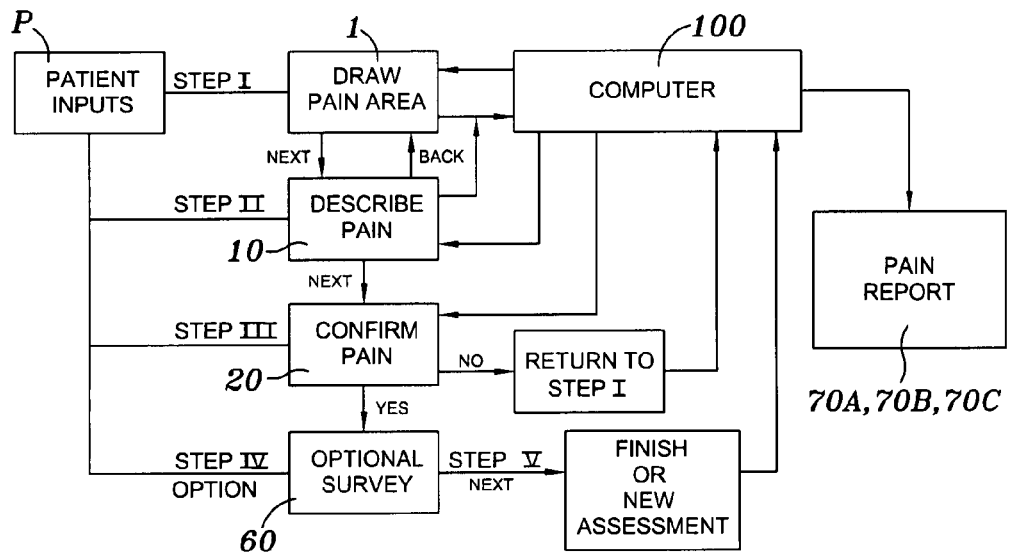
FIG. 5 is a block diagram illustrating the sequence of documenting a single pain area.
FIG. 6 is a typical survey with programmable questions and answers.

If the patient is totally satisfied with area and description of the pain, the patient clicks "next" and survey questions, up to eight, appear on screen 60, FIG. 6 (only five shown). The questions are programmed before the patient begins the computer pain assessment. The answers are entered by clicking the check "box" with the relevant answer which, like the questions, are programmed before the patient begins the computer pain assessment. The actual programmed answers would appear above each column of boxes instead of the numbers or as a legend for numbers 1-5 in FIG. 6, screen 60. If the patient does not want to complete the survey, the patient checks "next" and a screen appears with the options to go "back", a "new assessment" (start completely over) or click "finish". The data is saved by clicking "finish" on the navigation bar (not shown).

Referring now to FIG. 5, the block diagram delineates the sequences or steps that patient P performs in describing his or her pain with the computer pain assessment tool or method. For simplicity, FIG. 5 illustrates the sequences of interactive screens for patient P with a single area, type, intensity and depth of pain. Upon initiation or activation of computer 100 patient P observes screen 1 (see FIG. 1) and begins Step I drawing or shading the area of pain 8 on anterior 2 and posterior 3 of body replica 4. If patient P is satisfied with screen 1 as modified by his or her shading, then to start Step II patient P would click next and computer 100 would display screen 10 for patient P. In Step II patient P would respond by selecting in any order the intensity of pain by moving pointer A by dragging to or clicking on color spectrum intermediate pain intensity 12 and 13 on screen 10, FIG. 2; the type of pain, as preprogrammed, by checking the appropriate check box indicating the pain experience by patient P; and the depth of pain by moving pointer B by dragging to or clicking on the gray scale intermediate pain depth 18 and 19.

Patient P clicks next to begin Step III, computer 100 has processed the data inputs by patient P from Step I and Step II and displays screen 20 for confirmation of the pain. Patient P will either check box "yes" or box "no" to confirm or not to confirm, respectively, the pain. Upon checking "no" computer 100 displays screen 1 as originally completed by patient P for further modification. By clicking "next" computer 100 displays screen 10 as originally completed by patient P, then upon clicking "next" computer 100 has process the revision made in Step I and Step II and displays revised screen 20 for confirmation as revised.

When patient P clicks "yes" to confirm the pain, then "next", and begins Step IV where computer 100 displays survey screen 60, which patient P may complete or skip, then click "next", and go to Step IV where computer 100 displays a choice for patient P to indicate "finish", the assessment is completed and save data or indicate "new assessment" and all patient P data will be erased and screen 1, FIG. 1 will reappear for Step I to begin anew. Upon completion of the area and description of pain and confirming its accuracy using the computer pain assessment tool and then clicking "finish", computer 100 will process and store the patient's data and generate a pain report as illustrated in FIG. 7 for a first pain area, FIG. 8 for a second pain area, and FIG. 9 for the report summary. This report will indicate the intensity, type, depth and percentage of pain coverage (area) for the first and second pain area. The depth of pain is a number from zero to one hundred represented on the gray scale from white to black, respectively. The report will also include the Object Pain Value calculated from the intensity and pain coverage area.

The Objective Pain Value is a number devised from the fraction of the number of pixels shaded on body replica 4 over the total number of pixels forming body replica 4, then this fraction is multiplied by the pain intensity which is a number from zero to one hundred represented on the color spectrum scale from deep blue to red, respectively, to arrive at the Objective Pain Value. For example, referring to FIG. 7, screen 70A (ComPAT™ Report), the pain intensity was 46.23 on a scale of 0 to 100 and the pain coverage percent was 1.56% (pixels shaded divided by total body replica pixels) with the result being 0.72 (seventy-two hundredth) Objective Pain Value. To provide a more useful number, the pain coverage fraction would be multiplied by 100 rendering for this example, an Objective Pain Value of 72.

Referring to FIG. 7, screen 70A is the first page of the ComPAT™ Report for the first pain area 71 identified by vertical wavy lines on human body replica 72. The first page of the report would include patient information such as name, social security number, gender, date of birth, address, telephone, etc., as well as, height, weight, referral, surgery and/or injury date. For clarity this data is not presented in FIG. 7, screen 70A. FIG. 8, screen 70B is the second page of the report for the second pain area 75 identified by horizontal bars with interspersed slashes on human body replica 72. Indicia 71 marking the first pain area design indicates the type of pain (ache) and the color of the design indicates the pain intensity on a scale of 0 to 100 (46.23). Likewise, indicia 75 marking the second pain area design indicates the type of pain (stabbing) and the color of the design represents the intensity (80.04). The legends on screen 70A and 70B besides the intensity and type include the pain coverage percentage and the objective pain value. The legend on screen 70C, FIG. 9 combines the information on the legends on screens 70A and 70B to provide the total pain value, the average pain value, the average pain intensity, and the objective pain value.

For purposes of clarity in the FIGS. 1 through 4 and FIG. 6, the instructions on the computer screen display 1, 10, 20, 30 and 60 for the patient to follow, as well as, the navigation bar with the indicia, "Help", "Back", "Next" and "Finish" are not illustrated. These things are described as needed, and are not shown in the drawing to avoid complexity in illustrating the patient's pain assessment.

Although the invention has been shown and described with respect to a best mode embodiment thereof, it should be understood by those skilled in the art that various changes, omissions, and additions may be made to the form and detail of the disclosed embodiment without departing from the spirit and scope of the invention, as recited in the following claims.

What is claimed is:

1. A computer assisted system for objective assessment by a patient of a nature and extent of pain experienced by the patient comprising:
   a computer;
   a memory;
   a computer display screen;
   a user input device; and
   a computer program stored in the memory and executed by the computer to
   display a first interactive screen presentation of an anterior and a posterior image of a body replica containing a fixed quantity of pixels via the computer display screen;

shade on the first interactive screen presentation an area of the body replica representing a pain area based on information provided by the user input device, wherein a shaded number of pixels of the area of the body replica representing the pain area divided by the fixed quantity of pixels in the body replica defines a pain coverage;

display a second interactive screen presentation that depicts pain characteristics via the computer display screen, wherein the pain characteristics are associated with a color spectrum scale for indicating pain intensity, a preprogrammed list of pain types, and a gray scale for indicating a depth of pain;

indicate a pain intensity on the color spectrum scale in response to a first user input of at least one of dragging a pointer to and clicking on an intermediate color depicting the pain intensity between no pain and worst pain, wherein the color spectrum scale represents pain intensity on a numeric scale, with a color indicia corresponding to the numeric scale;

indicate the pain type from the preprogrammed list, wherein the pain type is associated with the pain area based on information provided by the user input device;

indicate the depth of pain on the gray scale in response to a second user input of at least one of dragging a marker to and clicking on an intermediate gray region depicting the depth of pain between superficial and deep;

display a third interactive screen presentation via the computer display screen, wherein the third interactive screen presentation comprises data from the first interactive screen presentation and the second interactive screen presentation to display the pain characteristics on the body replica with the pain type represented by a pattern associated with the pain type selected, the pain area represented by an area of the pattern, and the pain intensity represented by a color of the pattern;

display an option to confirm that the third interactive screen presentation accurately describes the pain experienced by the patient and an option to deny that the third interactive screen presentation accurately describes the pain experienced by the patient via the computer display screen;

redisplay the first interactive screen presentation for modification via the computer display screen in response to a selection of the option to deny;

present a final screen with an option for choosing to finish to save data associated with a current pain assessment and an option to start a new pain assessment in response to a selection of the option to confirm via the computer display screen; and compute an objective pain value from a number of pixels shaded on the first interactive screen presentation divided by the fixed quantity of pixels multiplied by the pain intensity on the numeric scale;

save the data and create a printable report in response to a selection of the option for choosing to finish.

2. The computer assisted system of claim 1 wherein the color spectrum scale represents pain intensity on a scale of zero to one hundred, with a corresponding color indicia of blue to red, respectively.

3. The computer assisted system of claim 1 wherein shading on the first interactive screen presentation is confined to the body replica.

4. The computer assisted system of claim 1 wherein the third interactive screen presentation further offers an option to choose an additional pain area to shade and describe.

5. The computer assisted system of claim 1 further comprising a fourth interactive screen presentation that offers an option to complete a preprogrammed questionnaire.

6. The computer assisted system of claim 1 wherein the type of pain is selected from a preprogrammed selection associated with a malady.

7. A method of computer documentation of patient data for prescribing therapy, including computer assisted self-assessment of pain by a patient, comprising:
displaying a first screen presentation of a human body replica with a fixed number of pixels defining an interactive area;
shading on the first screen presentation pixels of the human body replica where pain exists thereby representing a pain area, and wherein a shaded number of pixels of the area of the human body replica representing the pain area divided by the fixed number of pixels in the human body replica defines a pain coverage;
displaying a second screen presentation of selectable pain characteristics;
indicating on the second screen presentation pain characteristics where pain exists, wherein the selectable pain characteristics include a pain intensity indicated by a color spectrum scale having a corresponding numeric scale for measuring the pain intensity, a color indicia corresponding to the numeric scale, and wherein a number of the pixels of the body replica where pain exists divided by a number of pixels in the body replica multiplied by a number of the pain intensity on a scale of zero to one hundred defines an objective pain value;
displaying a third screen presentation based on first screen presentation data and second screen presentation data illustrating a pain area represented by an area of a pattern and pain characteristics experienced by the patient represented by a pattern associated with the pain characteristics and a pain intensity represented by a color of the pattern depicted on the body replica;
offering an option to acknowledge that the third screen presentation is an accurate pain assessment and an option to acknowledge that the third screen presentation is an inaccurate pain assessment;
displaying a fresh first screen presentation for starting an additional pain assessment in response to selection of the option to acknowledge that the third screen presentation is an accurate pain assessment; and
offering an option to finish a current pain assessment to save the current pain assessment and create a pain assessment report in response to selection of the option to acknowledge that the third screen presentation is an accurate pain assessment.

8. The method of claim 7 wherein selecting an additional pain assessment activates an additional pain assessment sequence.

9. The method of claim 7 wherein the selectable pain characteristics include the pain intensity, a type of pain, and a depth of pain.

10. The method of claim 9 wherein a gray scale represents the depth of pain on a scale of zero to one hundred, from the corresponding gray shade white to the corresponding gray shade black, respectively.

* * * * *